United States Patent
Wei et al.

(10) Patent No.: US 10,485,437 B2
(45) Date of Patent: Nov. 26, 2019

(54) LIGHT GUIDE SYSTEM FOR PHYSIOLOGICAL SENSOR

(71) Applicant: Bose Corporation, Framingham, MA (US)

(72) Inventors: Guang Wei, Southborough, MA (US); Harsh Anilkant Mankodi, Brighton, MA (US); Kimpon Ngem, Sturbridge, MA (US); Marko Orescanin, Framingham, MA (US); Shawn Prevoir, Northborough, MA (US)

(73) Assignee: BOSE CORPORATION, Framingham, MA (US)

( * ) Notice: Subject to any disclaimer, the term of this patent is extended or adjusted under 35 U.S.C. 154(b) by 1112 days.

(21) Appl. No.: 14/672,459

(22) Filed: Mar. 30, 2015

(65) Prior Publication Data
US 2016/0287108 A1    Oct. 6, 2016

(51) Int. Cl.
*A61B 5/02*    (2006.01)
*A61B 5/024*    (2006.01)
*A61B 5/00*    (2006.01)

(52) U.S. Cl.
CPC ...... *A61B 5/02427* (2013.01); *A61B 5/02433* (2013.01); *A61B 5/6817* (2013.01);
(Continued)

(58) Field of Classification Search
None
See application file for complete search history.

(56) References Cited

U.S. PATENT DOCUMENTS 8,700,111 B2    4/2014 LeBoeuf et al.
8,958,156 B1*   2/2015 Erdogan ............... G02B 5/288
                                            359/583
(Continued)

FOREIGN PATENT DOCUMENTS

JP    2011045458 A    3/2011
JP    2012518515 A    8/2012

OTHER PUBLICATIONS

International Preliminary Report on Patentability in International Patent Application No. PCT/US16/24741, dated Oct. 12, 2017; 7 pages.
(Continued)

*Primary Examiner* — Joel F Brutus
(74) *Attorney, Agent, or Firm* — Schmeiser, Olsen & Watts LLP; William G. Guerin

(57) ABSTRACT

A light guide system for a physiological sensor includes a light channel in optical communication with an emitter and a light channel in optical communication with a detector. The light channels are formed of a bio-compatible resilient plastic, such as a silicone, that is blended with a colorant. Each light channel has an optical transmission spectrum that passes the emitter spectral band and rejects most or all ambient light. The colorant can be a pigment provided as a suspension in a liquid or a dye provided in liquid form. The optical transmission spectrum defines a longpass optical filter where the shortest wavelength of the optical spectrum of the emitter is greater than the transition wavelength of the longpass optical filter. Each of the light channels is configured to be in contact with the skin, thereby reducing or eliminating optical loss due to transmission through an air gap.

22 Claims, 7 Drawing Sheets

(52) U.S. Cl.
CPC .......... *A61B 5/02438* (2013.01); *A61B 5/681* (2013.01); *A61B 5/6824* (2013.01); *A61B 5/6831* (2013.01); *A61B 2562/0233* (2013.01); *A61B 2562/185* (2013.01)

(56) References Cited

U.S. PATENT DOCUMENTS

| | | | |
|---|---|---|---|
| 2007/0279631 A1* | 12/2007 | Yershov | G01N 21/6454 356/417 |
| 2013/0131519 A1* | 5/2013 | LeBoeuf | A61B 5/0077 600/476 |
| 2013/0161538 A1* | 6/2013 | Mei | B01J 19/121 250/492.1 |
| 2013/0324854 A1* | 12/2013 | Alley | A61B 5/441 600/473 |
| 2015/0031967 A1 | 1/2015 | Leboeuf et al. | |
| 2015/0073236 A1 | 3/2015 | Leboeuf et al. | |

OTHER PUBLICATIONS

International Search Report & Written Opinion in counterpart International Patent Application No. PCT/US16/24741, dated Jun. 13, 2016; 11 pages.
Office Action in Japanese Patent Application No. 2017-551256 dated Oct. 5, 2018; 6 pages.

\* cited by examiner

LIGHT GUIDE SYSTEM FOR PHYSIOLOGICAL SENSOR

BACKGROUND

Physiological sensors such as heart rate sensors based on one or more emitters and detectors have been developed for use in monitoring health and exercise. These sensors are sometimes integrated into an earbud or other wearable form intended for positioning close to or against the skin of a wearer. Such devices often cause discomfort to the wearer when moving or during exercise, and may exhibit degraded performance due to ambient light.

SUMMARY

In one aspect, light guide system for a physiological sensor having an emitter and a detector includes a pair of light channels. Each of the light channels is formed of a bio-compatible resilient plastic and is configured for contact with the skin of a wearer. One of the light channels is in optical communication with the emitter and the other light channel is in optical communication with the detector. The bio-compatible resilient plastic has an optical transmission spectrum that transmits the optical energy of the emitter and substantially blocks ambient light.

Embodiments of the light guide system may include one of the following features, or any combination thereof. The optical transmission spectrum may define a longpass optical filter where a lowest wavelength of an optical spectrum of the emitter is greater than a transition wavelength of the longpass optical filter. The bio-compatible resilient plastic can be a dyed silicone. The light channels can be in different structures such as a wristband, finger band, watch, chest strap, arm band, necklace or an eartip for an earbud.

In another aspect, a physiological sensor includes a sensor body, an emitter, a detector, a processor and a pair of light channels. The emitter is disposed in the sensor body and is configured to irradiate a skin of a wearer with an optical beam. The detector is disposed in the sensor body and is configured to receive optical energy from the irradiated skin of the wearer and to generate an electrical signal in response to the received optical energy. The processor is in communication with the detector and is configured to determine physiological data for the wearer in response to the electrical signal. Each light channel is formed of a bio-compatible conformable plastic and is configured for contact with the skin of the wearer. One of the light channels is in optical communication with the emitter and the other light channel is in optical communication with the detector. The bio-compatible conformable plastic has an optical transmission spectrum that transmits the optical energy of the emitter and substantially blocks ambient light.

Embodiments of the physiological sensor may include one of the above and/or below features, or any combination thereof. The emitter can be a light emitting diode. The physiological sensor may further include an eartip that is attachable to the earbud and in which the pair of light channels is disposed. The sensor body can be a wristband, finger band, watch, chest strap, arm band, necklace or an earbud.

In another aspect, a light guide system for a physiological sensor includes an emitter, a detector and an eartip. The emitter is configured to irradiate a skin of a wearer with an optical beam. The detector is configured to receive optical energy from the irradiated skin of the wearer and to generate an electrical signal in response to the received optical energy. The eartip has an eartip body and a pair of light channels integrally molded into the eartip body. Each light channel is formed of a bio-compatible resilient plastic and is configured for contact with the skin of a wearer. One of the light channels is in optical communication with the emitter and the other light channel is in optical communication with the detector. The bio-compatible resilient plastic has an optical transmission spectrum that transmits the optical energy of the emitter and substantially blocks ambient light.

Embodiments of the light guide system for a physiological sensor may include one of the above and/or below features, or any combination thereof. The optical transmission spectrum may define a longpass optical filter where a lowest wavelength of an optical spectrum of the emitter is greater than a transition wavelength of the longpass optical filter. The bio-compatible resilient plastic can be a dyed silicone.

BRIEF DESCRIPTION OF THE DRAWINGS

In the following description, reference is made to accompanying drawings in which like reference numerals indicate like elements and features in the various figures. For clarity, not every element may be labeled in every figure. The drawings are not necessarily to scale, emphasis instead being placed upon illustrating certain principles.

DETAILED DESCRIPTION

Figure 1:
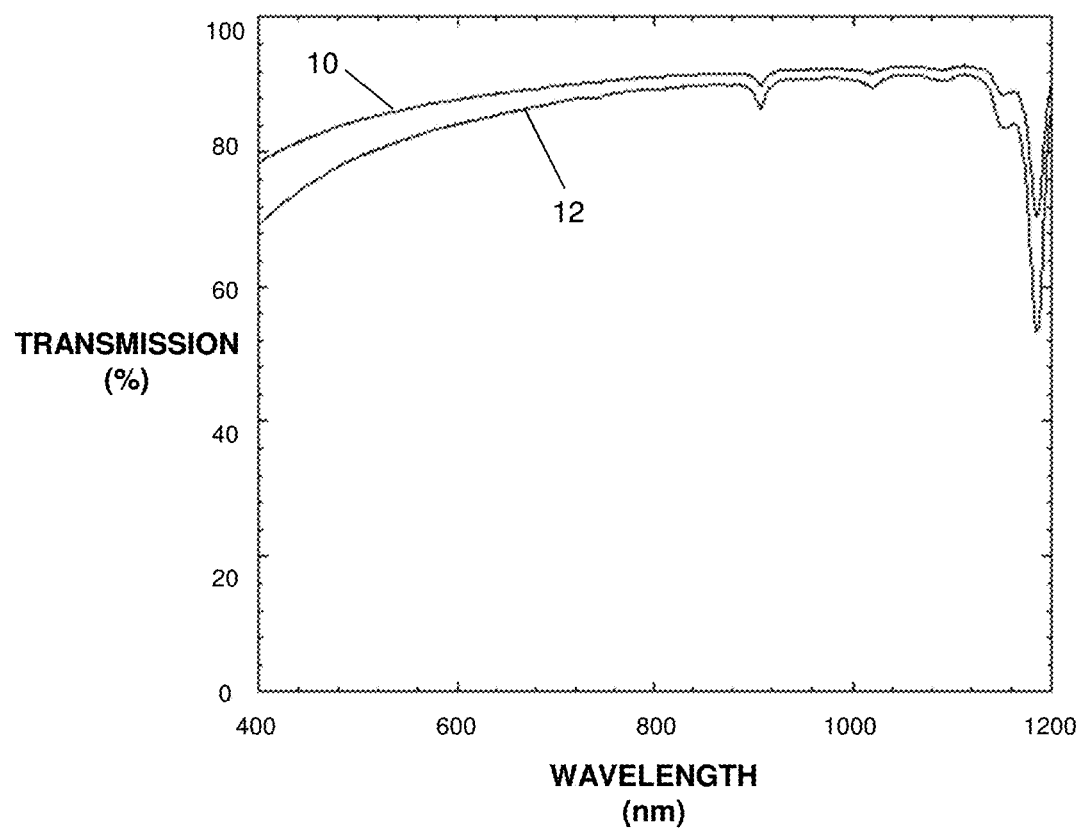
FIG. 1 is a graph of optical transmission as a function of wavelength for 1.72 mm and 3.35 mm thick samples of translucent silicone.

The terminology used herein is for the purpose of describing particular examples and implementations only and is not intended to be limiting. All terms used herein have the same meaning as commonly understood by one of ordinary skill in the art unless defined otherwise herein.

The term "physiological" refers to characteristics of the functions of a human or animal body. The term "skin" as used herein refers generally to the skin of a human or animal and includes surfaces of the internal and external features of the ear. A "bio-compatible" material means any material that exhibits substantially no adverse effect when in contact with skin. For example, a bio-compatible material is not toxic, not abrasive to skin, chemically inert with respect to skin, non-allergenic and does not cause discomfort to a human or animal.

The term "sensor" as used herein refers to a device that detects or senses energy (e.g., heat, light, sound and the like) and generates a signal responsive to a parameter (e.g., temperature, intensity, acoustic pressure and the like) of the detected energy. For example, an optical sensor detects optical energy and can generate a signal responsive to a parameter (e.g., intensity) of the light incident on the sensor. In some examples described below, a sensor includes a combination of components, including an emitter to generate optical energy and a detector to detect optical energy.

A "monitor" as used herein refers to a device for monitoring, or observing, a detected parameter. In some implementations and examples described below, a monitor includes a sensor and generates an output, such as a display or audio signal that can be observed or heard, based on a signal generated by the sensor.

The term "body" refers generally to an object or structure. The body may include features to allow one or more components to be disposed inside the body (e.g., embedded within the body or disposed in a body cavity), on the surface of the body, or attached to the body using fasteners or connectors, or through one or more intervening structures.

The term "earbud" refers to an earphone that is at least partially insertable into an ear. Earbuds also include canalphones and similar devices. The term "eartip" is synonymous to the term "earbud tip" and refers to a removable and replaceable component that is attachable to the body of an earbud. The eartip may be used to seal the ear canal from ambient sound.

Physiological monitors for the general public have become popular in recent years. These monitors are often in the form of a wearable fitness tracking device, such as a wristband, or they may be integrated into a device providing additional functionality. Sensors for physiological monitors may be worn at any of a variety of locations on the body, including the wrist, chest, finger, arm and neck. Specific examples include earbuds and watches having heart rate sensors that enable a wearer to monitor their heart rate while serving their primary function of presenting audio output or a time display to the wearer.

One type of heart rate sensor is based on an optical technique in which light from one or more optical emitters, such as a light emitting diode (LED), irradiates the skin of the wearer. Some of the light may be reflected from the irradiated skin while some of the light penetrates below the surface of the skin into tissue which typically includes vascular structure such as veins, arteries, capillaries and the like. A majority of the light backscattered from below the skin surface is typically time-invariant; however, the intensity of backscattered light from blood typically varies in time. This time variation is caused by changes in the optical absorption spectrum of the blood due to oxygenation variations for each pulse. The intensity variation can also be based on a variation in the volume of blood exposed to the light during each pulse. An optical detector receives a portion of the backscattered light and generates a signal having a constant (DC level) component and a time-variant (AC level) component. The signal is first provided to an analog front end (AFE) for preconditioning or directly to a processor which determines the heart rate of the wearer from the dominant frequency of the time-variant component of the signal.

Heart rate sensors may be worn at a location on the body where the time-variant component of the signal is significant. Heart rate sensors typically have at least one LED emitter and one or more optical detectors. The emitter and detector are typically located inside or on a sensor body. For example, the sensor body can be an earbud. A first region extending from the emitter to the surface of the sensor body and a second region extending from the detector to the surface of the sensor body are typically formed as a hard plastic, such as polycarbonate, that permits the transmission of light in the near infrared (NIR) spectrum and at least a portion of the visible spectrum. Generally, the two regions are separated from each other by an opaque region that prevents the direct passage of light between the two regions. In some instances, the hard plastic extends beyond the surface of the sensor body and is configured to be in direct contact with the skin. The processor is typically located remote to the sensor body and is in electrical communication with the sensor through a cable having one or more wires.

A heart rate sensor in an earbud may be offset from the irradiated skin in the ear so that much of the optical energy from the emitter is lost through attenuation in the air gap and due to reflection at the refractive index discontinuities at the interface of the ear tissue and air and at the interface of the hard plastic and air. The signal to noise ratio (SNR) of the AC level component of the signal, i.e., the modulated optical energy incident on the detector, degrades according to increasing loss of the optical energy. Heart rate monitors and other physiological monitors based on optical irradiation of skin and detection of the backscattered and reflected light can be further adversely affected during exercise or other physical activities. More specifically, when the wearer is in motion, the positions of the emitter and detector relative to the skin can change. For example, the position of an earbud within the ear of a wearer may shift frequently during running or other forms of exercise.

The optical loss due to transmission of light through air limits the acceptable separation of the sensor from the skin and generally results in a requirement for more optical power as the separation increases, although the optical loss at the refractive index discontinuities remains substantially constant. In addition, the presence of the air gap provides a means for ambient light to reach the detector and thereby decrease the SNR. The earbud body can be increased in size to eliminate the air gap; however, the contact of the hard body against the ear can cause discomfort to the wearer, including soreness or pain after long term use. The SNR of the detected optical signal can be improved by increasing the optical energy; however, increasing the optical power of the emitter can decrease the battery life of the device. Moreover, if the sensor resides in a recessed portion of the earbud body, dust may gather over time and ear wax or salt from perspiration can collect in the recessed portion. As a result, optical signal transmission can decrease.

Eartips are sometimes used with earbuds to seal the ear canal from the ambient environment and to stabilize the location of the earbud with respect to the ear. An opening in the eartip passes the acoustic energy to the inner ear while the contact seal between the eartip and the ear canal aids in the reduction or elimination of background acoustic noise heard by the wearer. Eartips are typically formed from materials that are comfortable to wear, including soft polymers such as silicone which can conform to complex ear shapes and canals.

FIG. 1 shows optical transmission with respect to wavelength for 1.72 mm and 3.35 mm thick samples (plots 10 and 12, respectively) of translucent silicone that may be used for an eartip. High transmission without significant variation is observed throughout the visible spectrum and in the near infrared (NIR) spectrum up to approximately 1150 nm. Silicone is recognized for its safety for contact with human tissue and its comfort for earbud users; however, the broad transmission spectrum, which includes the visible spectrum and NIR wavelengths below the spectrum of the emitter, enables ambient light to reach the detector and degrade the SNR of the heart rate sensor.

In certain examples of a light guide system for a physiological sensor described herein, the system includes a light channel in optical communication with an emitter and a light channel in optical communication with a detector. The light channels are formed of a bio-compatible resilient plastic, such as a silicone, that is blended with a colorant. Each light channel has an optical transmission spectrum that passes the emitter spectral band and rejects most of the optical energy at shorter wavelengths. The colorant can be a pigment provided as a suspension in a liquid. Alternatively, the colorant can be a dye provided in liquid form. In some implementations the colorant is a mixture of pigments, a mixture of dyes or a mixture having at least one dye and at least one pigment.

In effect, the optical transmission spectrum defines a longpass optical filter where the shortest wavelength of the optical spectrum of the emitter is greater than the transition wavelength of the longpass optical filter. As used herein, "transition wavelength" means the shortest wavelength of the broad transmission region at which transmission is 50% of the maximum transmission. Each of the light channels is configured to be in contact with the skin, thereby reducing or eliminating optical loss due to transmission through air.

In an alternative example, the emitter may be a narrow band optical source such as a laser diode. As described above, the light channels can have an optical transmission spectrum that passes the emitter spectral band and rejects most of the optical energy at shorter wavelengths. Alternatively, the light channels can have a narrow band optical transmission spectrum that passes the narrow laser diode spectral band and rejects most of the optical energy at wavelengths below and above the spectral band of the emitter.

Figure 2:
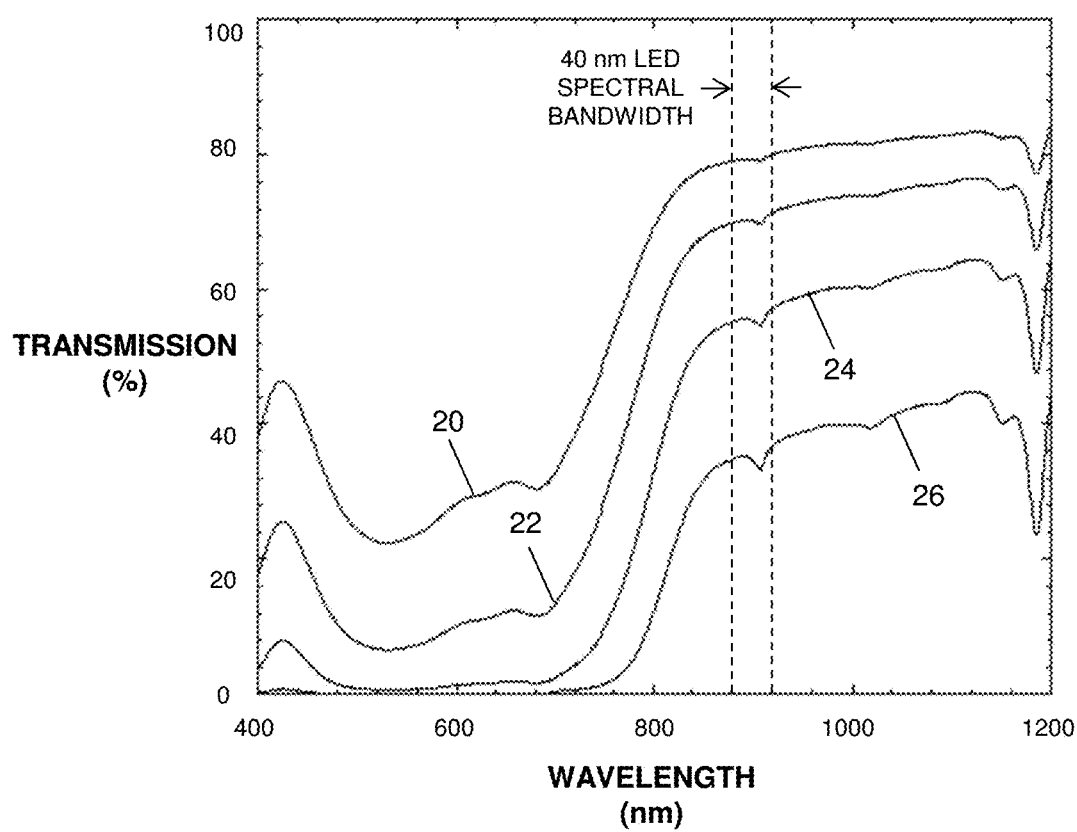
FIG. 2 is a graph of optical transmission as a function of wavelength for a blend of silicone and Lumogen® Black 4280 pigment at a 2% pigment concentration.

By way of a specific and non-limiting example for light channels having a longpass optical filter characteristic, FIG. 2 shows the optical transmission property of a blend of silicone and Lumogen® Black 4280 pigment (available from BASF Corporation of Charlotte, N.C.) at a 2% pigment concentration. The blended material can be used as a suitable material for each light channel. Plots 20, 22, 24 and 26 represent the blended silicone samples at thicknesses of 0.45 mm, 0.85 mm, 1.66 mm and 3.31 mm, respectively. For all thicknesses, the corresponding transition wavelength is less than the shortest wavelength of the spectral band of a typical emitter for an optically-based heart rate monitor. For example, an LED emitter may have a central wavelength of approximately 900 nm with a full width half maximum (FWHM) spectral bandwidth of approximately 40 nm. In this example, an optical transmission spectrum having a transition wavelength of close to but less than 880 nm is preferred for maximum rejection of background light.

In one technique, the colorant is provided as a liquid that is mixed with liquid silicone rubber (LSR) in gel form. The mixture is injected into a mold to form a resilient silicone object having a desired shape. The resulting light channels can be molded into a larger integral molded body such as an eartip for an earbud. In other implementations of light guide systems for physiological sensors, other bio-compatible resilient plastics are used for the light channels as long as the optical transmission spectrum of the plastic material passes the optical energy of the emitter and substantially blocks ambient light. Thus, various pigments and dyes can be mixed with various plastic materials to achieve a desired optical transmission spectrum.

In various implementations, the physiological sensor is a heart rate sensor located within or on an earbud. More specifically, the body of the earbud serves as the sensor body and the sensor includes an emitter and a detector.

In various examples, the light channels are formed as part of an eartip that can be attached to and removed from the earbud body. When the eartip is attached, one of the light channels is located over the emitter and the other light channel is located over the detector. The cross-sectional area of each light channel may be selected according to the dimensions of the active areas of the emitter and detector. In some examples described below, more than one light channel is used to propagate light from one or more emitters and/or one or more light channels is used to provide light to one or more detectors.

Figure 3:
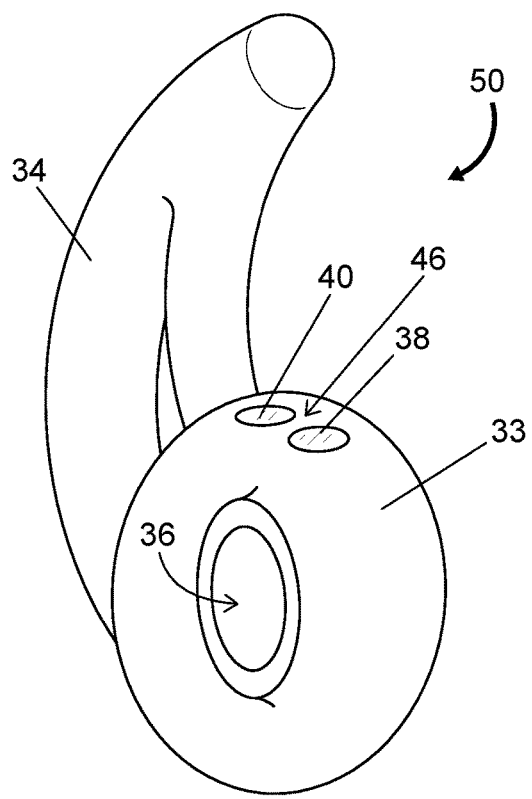
FIG. 3 is a perspective illustration of an example of a left ear tip for an optical heart rate sensor disposed in an earbud body.

FIG. 3 is a side view illustration of a left ear tip 50 for an optical heart rate sensor disposed in an earbud body. The body 33 of the eartip is formed of a resilient plastic such as silicone that is modified to be opaque in the visible and NIR spectrum. A positioning and retaining structure 34 extending from the eartip body 33 provides a means of maintaining an earbud attached to the eartip body 33 in a stationary position relative to the ear canal. The positioning and retaining structure 34 may be formed of a hard plastic or formed of the same resilient plastic as the eartip body 33, and may be either transparent or opaque. An opening 36 through the eartip body 33 provides a means for the acoustic signal generated by an attached earbud to propagate into the ear canal. A pair of light channels 38 and 40 is located at the top of the eartip 30. The light channels 38 and 40 are formed of a resilient plastic that has an optical transmission spectrum to permit optical energy from the emitter to pass through the eartip 30 to the ear and to permit optical energy backscattered from the irradiated region of the ear to pass through the eartip 50 to the detector. When the body 33 of the eartip 50 is attached to an earbud, the back end (not visible) of one light channel 38 is configured to be in contact with a protective transparent cover disposed over the emitter. Similarly, the back end of the other light channel 40 is configured to be in contact with a protective cover disposed over the detector. As illustrated, a portion 46 of the eartip body 33 is located between the two light channels 38 and 40. This opaque portion 46 prevents light from the emitter from having a direct optical path to the detector.

Figure 4:
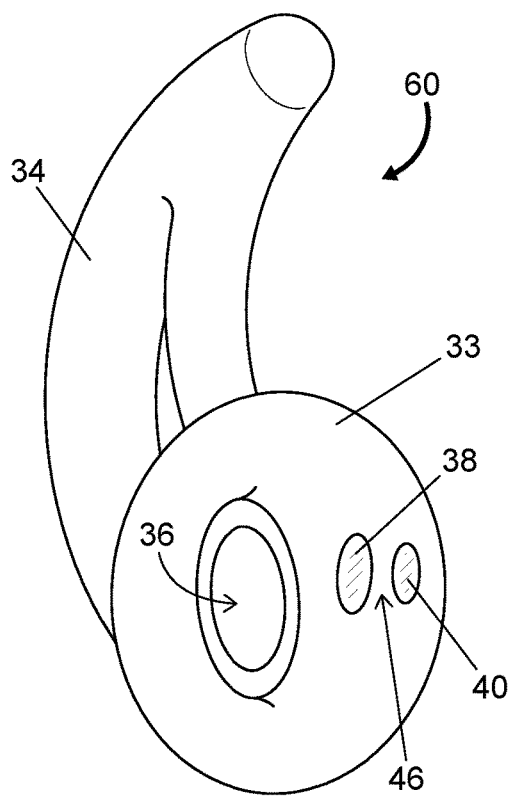
FIG. 4 is a perspective illustration of an example of a left eartip for an optical heart rate sensor in an earbud body.
Figure 5:
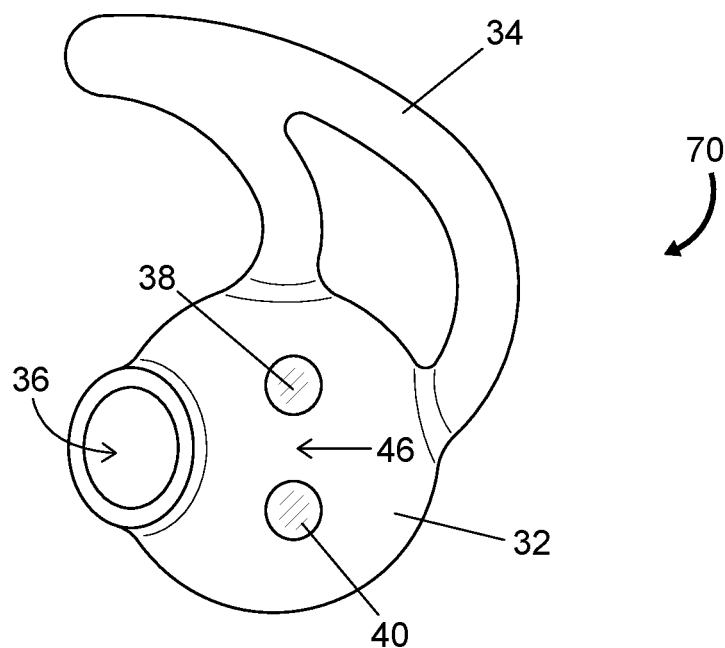
FIG. 5 is a perspective illustration of an example of a right eartip for an optical heart rate sensor in an earbud body.

FIG. 4 and FIG. 5 are perspective illustrations of examples of a left eartip 60 and a right ear tip 70 for an optical heart rate sensor in an earbud body. The eartips 60 and 70 are shaped similarly to the left eartip 50 shown in FIG. 3; however, the light channels 38 and 40 are at different locations on the eartip body 33 and 32, respectively. In particular, FIG. 4 shows the light channels 38 and 40 located on the opposite side of the acoustic opening 36 with respect to the positioning and retaining structure 34. FIG. 5 shows the light channels 38 and 40 being vertically separated and located between the acoustic opening 36 and the positioning and retaining structure 34. In both illustrated examples, the exposed ends of the two light channels 38 and 40 are configured for contact with the neighboring structure of a human ear.

Figure 6:
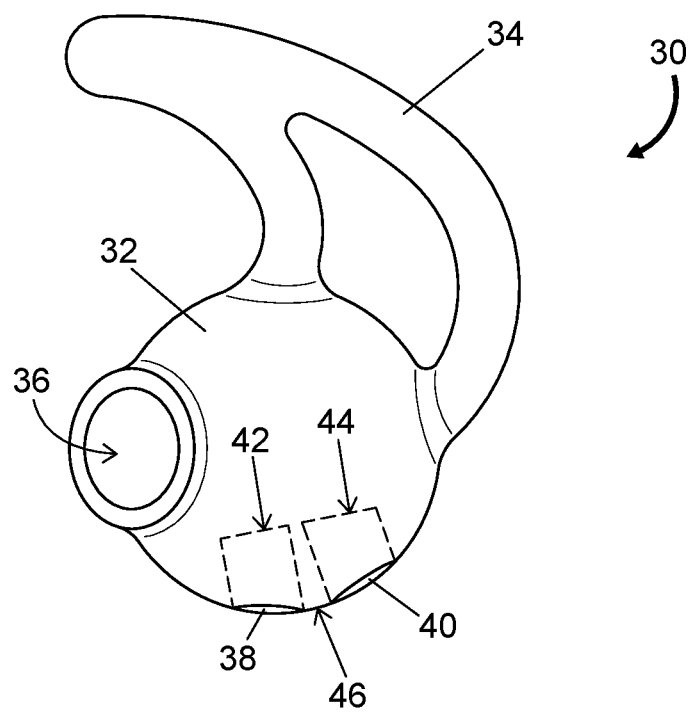
FIG. 6 is a perspective illustration of another example of a right eartip for an optical heart rate sensor in an earbud body.

FIG. 6 is a perspective illustration of another example of a right eartip 30. The two light channels 38 and 40 are located on the bottom of the eartip body 32 and separated by a portion 46 of the eartip body 32.

Figure 7:
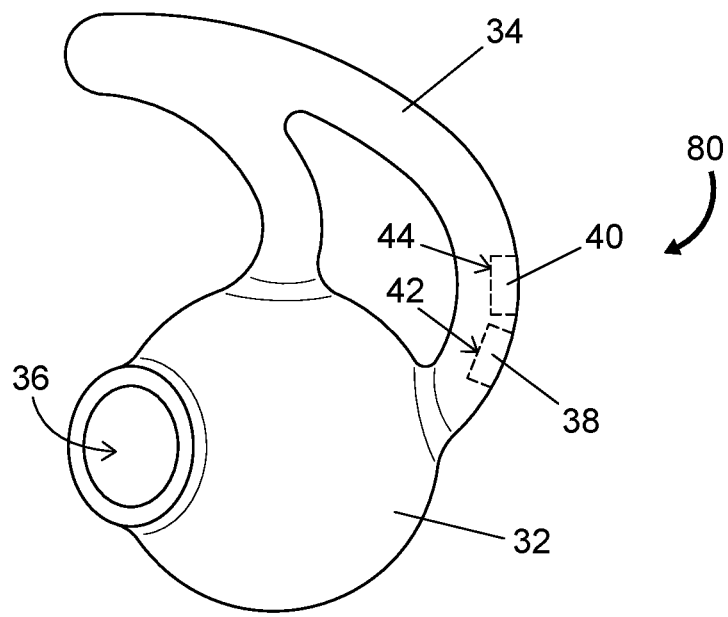
FIG. 7 is a perspective illustration of another example of a right eartip for an optical heart rate sensor in an earbud body where a positioning and retaining structure is shown as a cut-away view.

FIG. 7 is a perspective illustration of another example of a right eartip 80 where the positioning and retaining structure 34 is shown as a cut-away view to depict how the light channels 38 and 40 are located in the positioning and retaining structure 34. In this example the emitter and detector (not shown) are disposed substantially adjacent to the end 42 or 44 of a respective one of the light channels 38 and 40, respectively. The light channels 38 and 40 are located such that the light from the emitter irradiates a portion of the antihelix of the ear.

Figure 8:
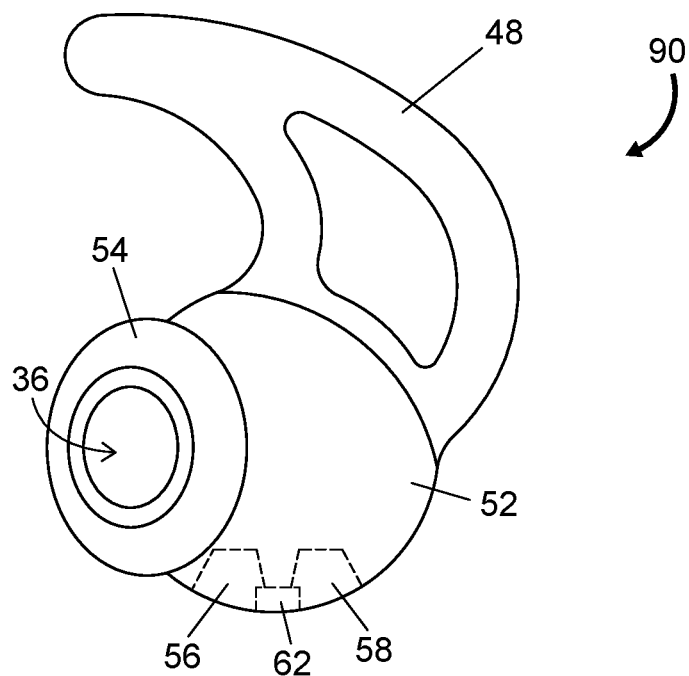
FIG. 8 is a perspective illustration of another example of a right eartip for an optical heart rate sensor in an earbud body.

FIG. 8 is a perspective illustration of another example of a right eartip 90. In this example, the positioning and retaining structure 48 is a separate element that is attached to an earbud body 52. A removable version of the positioning and retaining structure may be used with any of the examples described above. The third element in the illustration is an umbrella eartip 54 that is attached to the earbud body 52, which may be used with any of the examples described above. In this example, the light channels 38 and 40 are located in the earbud body 52 and extend to or beyond the body surface. For manufacturing purposes, the light channels 38 and 40 may be formed as individual plugs where each plug is inserted into an opening in the earbud body 52. In an alternative example, two light channels 56 and 58 are coupled together at one end into a single element by a bridge portion 62. Preferably, the bridge portion 62 is selectively formed of pigment or dye to be opaque with respect to the optical spectrum of the emitter and thereby eliminate a direct optical path from the emitter to the detector.

FIGS. 9A to 9F show end view illustrations of a number of light channel configurations that may be used according to various implementations.

Figure 9A:
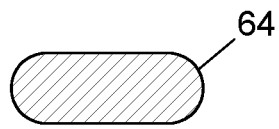
FIGS. 9A to 9F are end view illustrations of a number of light channel configurations for a light guide system that may be used in various implementation of a physiological sensor.

FIG. 9A shows a single light channel 64 that may be used if cross talk between the emitter and the detector is not significant. Preferably, the separation between the emitter and detector is increased in comparison to other implementations to reduce crosstalk. In an extension of this variation, the entire eartip is made of long-pass silicone for simplicity of manufacture. In another variation, the central portion of the single light channel may be made opaque so that the single piece operates as two independent light channels. Alternatively, if the entire eartip is made of the long-pass dyed silicone, a region separating the optical paths for the emitter and detector may be made opaque to reduce or eliminate crosstalk.

Figure 9B:
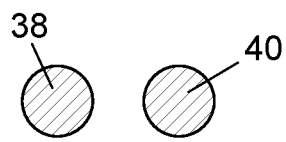

FIG. 9B show a separation of the two light channels 38 and 40 as described above for various examples.

Figure 9C:
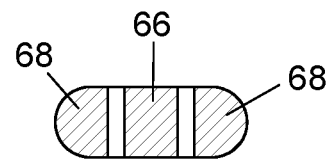
Figure 9D:
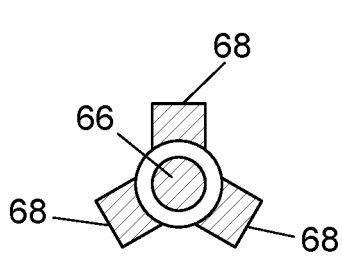
Figure 9E:
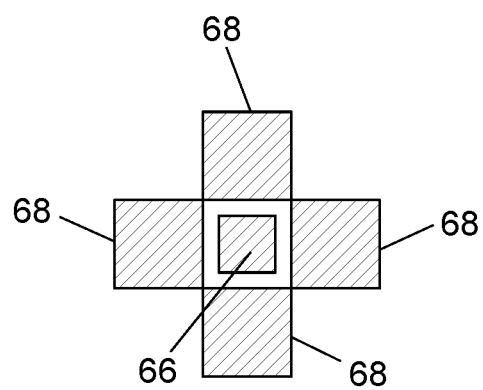

FIGS. 9C, 9D and 9E show a central light channel 66 adapted for optical communication with an emitter with multiple light channels 68 surrounding the central light channel 66 and adapted for optical communication with one or more detectors.

Figure 9F:
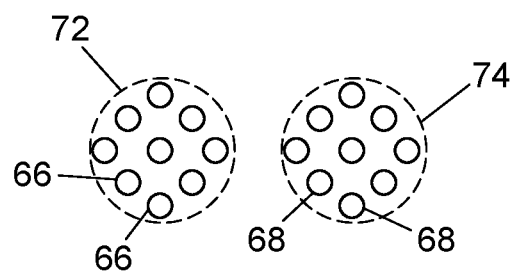

FIG. 9F illustrates a group 72 of light channels 66 configured for optical communication with multiple emitters and a second group 74 of light channels 68 configured for optical communication with multiple detectors. The illustrated groupings of light channels 66 can be advantageous for implementations into ear tips having complex geometries. In some implementations, less dyed or pigmented material is used. In other implementations, the groupings permit information averaging or multiple measurements to be obtained and averaged.

Figure 10:
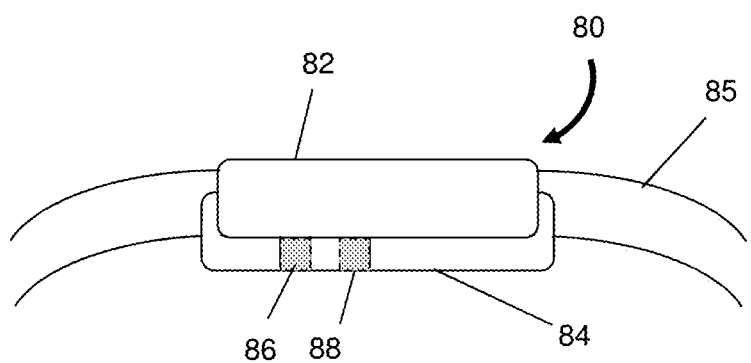
FIG. 10 is an illustration of an example of a watch case disposed on a silicone bottom layer having two light channels for use with a physiological sensor disposed in the watch case.

The various examples described above are directed to an eartip for an earbud. FIG. 10 shows an example of a watch case 80 in which a watch case body 82 is disposed on a silicone bottom layer 84. Two light channels 86 and 88 having similar transmission properties to the light channels in the examples described above are located in the silicone bottom layer 84 and are used in conjunction with an optical physiological sensor, such as a heart rate monitor, located in the watch case body 82.

Figure 11:
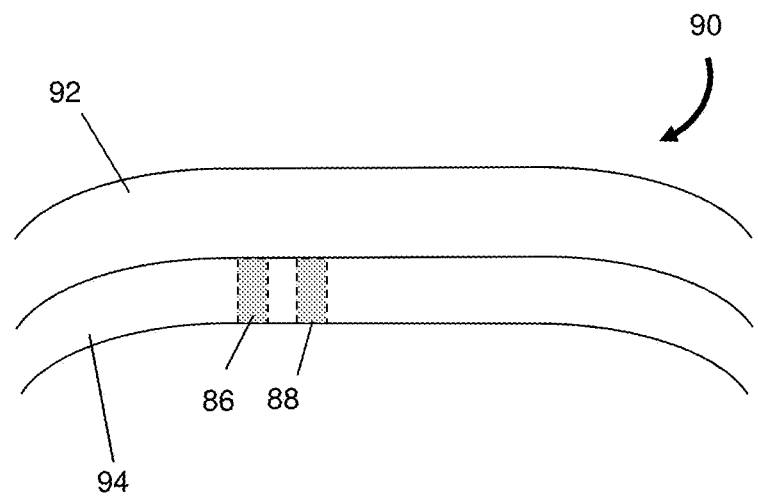
FIG. 11 is an illustration of an example of a wrist band having a band body and a silicone bottom layer with two light channels for use with a physiological sensor disposed in or on the band body.

FIG. 11 shows an example of a wrist band 90, such as a watch band, that includes a band body 92 with a silicone bottom layer 94. Two light channels 86 and 88, similar to those shown for the watch case 80 of FIG. 10, allow for passage of the optical energy emitted from and returned to an optical physiological sensor disposed in or on the band body 92.

In general, light guide systems for physiological sensors according to the principles described herein enable improved performance and provide for wearer comfort. A number of implementations and examples have been described. Nevertheless, it will be understood that additional modifications may be made without departing from the principles described herein. For example, the size, location and number of light channels can differ from those described above in the various implementations.

What is claimed is:

1. A light guide system for a physiological sensor having an emitter and a detector, the light guide system comprising a pair of light channels, each of the light channels formed of a bio-compatible plastic and configured for contact with the skin of a wearer, one of the light channels being in optical communication with the emitter and the other light channel being in optical communication with the detector, the bio-compatible plastic having an optical transmission spectrum that transmits the optical energy of the emitter and substantially blocks ambient light.

2. The light guide system of claim 1 wherein the optical transmission spectrum defines a longpass optical filter and wherein a shortest wavelength of an optical spectrum of the emitter is greater than a transition wavelength of the longpass optical filter.

3. The light guide system of claim 2 wherein the transition wavelength of the longpass optical filter is less than 880 nm.

4. The light guide system of claim 1 wherein the bio-compatible plastic is a dyed silicone.

5. The light guide system of claim 1 wherein the emitter and the detector are disposed in an earbud.

6. The light guide system of claim 1 wherein the light channels are disposed in an eartip for an earbud.

7. The light guide system of claim 6 wherein the light channels and eartip are formed as an integral molded body.

8. The light guide system of claim 6 wherein the light channels and the eartip are formed of the same bio-compatible plastic.

9. The light guide system of claim 8 wherein the light channels comprise a dyed silicone and the eartip comprises the same silicone without the dye.

10. The light guide system of claim 6 wherein the light channels are formed as plugs that are located in openings in the eartip.

11. The light guide system of claim 1 further comprising a bridge portion that extends between one end of each of the light channels and is formed of the bio-compatible plastic.

12. The light guide system of claim 11 wherein the light channels are embedded in an earbud body and each of the light channels extends at one end from a respective one of the emitter and the detector and wherein the bridge portion is disposed along a surface of the earbud body.

13. A physiological sensor comprising:
a sensor body;
an emitter disposed in the sensor body and configured to irradiate a skin of a wearer with an optical beam;
a detector disposed in the sensor body and configured to receive optical energy from the irradiated skin of the wearer and to generate an electrical signal in response to the received optical energy;
a processor in communication with the detector and configured to determine physiological data for the wearer in response to the electrical signal; and
a pair of light channels each formed of a bio-compatible conformable plastic and configured for contact with the skin of the wearer, one of the light channels being in optical communication with the emitter and the other light channel being in optical communication with the detector, the bio-compatible conformable plastic having an optical transmission spectrum that transmits the optical energy of the emitter and substantially blocks ambient light.

14. The physiological sensor of claim 13 wherein the sensor body is an earbud.

15. The physiological sensor of claim 14 further comprising an eartip that is attachable to the earbud and wherein the pair of light channels is disposed in the eartip.

16. The physiological sensor of claim 13 wherein the emitter is a light emitting diode (LED).

17. The physiological sensor of claim 13 wherein the sensor body is part of one of a watch, wristband, finger band, chest strap, arm band and necklace.

18. The physiological sensor of claim 13 wherein the physiological data are heart rate data.

19. A light guide system for a physiological sensor comprising:
an emitter configured to irradiate a skin of a wearer with an optical beam;
a detector configured to receive optical energy from the irradiated skin of the wearer and to generate an electrical signal in response to the received optical energy; and
an eartip having an eartip body and a pair of light channels integrally molded into the eartip body, each of the light channels formed of a bio-compatible plastic and configured for contact with the skin of a wearer, one of the light channels being in optical communication with the emitter and the other light channel being in optical communication with the detector, the bio-compatible plastic having an optical transmission spectrum that transmits the optical energy of the emitter and substantially blocks ambient light.

20. The light guide system of claim 19 wherein the optical transmission spectrum defines a longpass optical filter and wherein a shortest wavelength of an optical spectrum of the emitter is greater than a transition wavelength of the longpass optical filter.

21. The light guide system of claim 19 wherein the bio-compatible plastic is a dyed silicone.

22. The light guide system of claim 19 wherein the electrical signal is indicative of a heart rate of the wearer.

* * * * *